(12) United States Patent
Hu et al.

(10) Patent No.: US 7,531,316 B2
(45) Date of Patent: May 12, 2009

(54) HIGH THROUGHPUT ASSAY OF LP-PLA2 ACTIVITY

(75) Inventors: Yun-Fu Hu, Research Triangle Park, NC (US); George T. Walker, Research Triangle Park, NC (US)

(73) Assignee: Glaxo Group Limited, Greenford, Middlesex (GB)

( * ) Notice: Subject to any disclaimer, the term of this patent is extended or adjusted under 35 U.S.C. 154(b) by 145 days.

(21) Appl. No.: 10/557,540

(22) PCT Filed: May 27, 2004

(86) PCT No.: PCT/US2004/016716

§ 371 (c)(1),
(2), (4) Date: Nov. 21, 2005

(87) PCT Pub. No.: WO2005/001416

PCT Pub. Date: Jan. 6, 2005

(65) Prior Publication Data

US 2007/0065892 A1 Mar. 22, 2007

Related U.S. Application Data

(60) Provisional application No. 60/473,777, filed on May 28, 2003.

(51) Int. Cl.
*C12Q 1/34* (2006.01)
(52) U.S. Cl. .......................... 435/18; 435/198
(58) Field of Classification Search .................. 435/18, 435/13, 69.2, 198
See application file for complete search history.

(56) References Cited

U.S. PATENT DOCUMENTS

| | | | |
|---|---|---|---|
| 5,698,403 | A | 12/1997 | Cousens et al. |
| 5,981,252 | A | 11/1999 | MacPhee et al. |
| 6,203,790 | B1 | 3/2001 | Cousens et al. |
| 2002/0102231 | A1 | 8/2002 | Dietsch et al. |
| 2003/0072747 | A1 | 4/2003 | Cousens et al. |
| 2003/0148398 | A1 | 8/2003 | McPhee et al. |
| 2005/0244913 | A1 | 11/2005 | Shou et al. |
| 2007/0166777 | A1* | 7/2007 | Shou et al. ................ 435/15 |

FOREIGN PATENT DOCUMENTS

| | | |
|---|---|---|
| EP | 816504 A2 | 1/1998 |
| EP | 1318154 A1 | 6/2003 |
| JP | 06116279 A | 4/1994 |
| JP | 07059597 | 3/1995 |
| JP | 2002-179545 | 6/2002 |
| WO | WO 9509921 A1 | 4/1995 |
| WO | WO00/32808 A1 | 5/2000 |
| WO | WO2004/089184 A1 | 10/2004 |
| WO | WO2005/001416 A2 | 1/2005 |
| WO | 2005/074604 A2 | 8/2005 |

OTHER PUBLICATIONS

Alexandros D Tselepis; PAF-degrading acetylhydrolase is preferentially associated with dense LDL and VHD-1 in human plasma; catalytic characteristics and relation to the monocyte-derived enzyme.; Arteriosclerosis Thrombosis and Vascular Biology; 1995; 15(10); 1764-1773.
Palmantier R et al; Biosynthesis of PAF-Acether XIV. PAF-Acether Output in Murine Peritoneal Macrophages is regulated by the level of acetylhydrolase; Biochemical and Biophysical Research Communications; 1989; 162, No. 1; 475-482.
D M Stafforini; Platelet—activating factor acetylhydrolase from human plasma; Methods in Enzymology, Academic Press Inc, San Diego, CA, US; 1990; 187; 344-357.
Petrovic Nenad et al; A simple assay for a human serum phospholipase A2 that is associated with high-density lipoproteins; Journal of Lipid Research; Oct. 2001; 42 (10); 1706-1713.
Min J., et al., "Platelet Activating Factor Acetylhydrolases: Broad Substrate Specificity and Lipoprotein Binding does not Modulate the Catalytic Properties of the Plasma Enzyme," *Biochemistry* 40(15):4539-4549 (2001).
Kosaka T., et al., "Serum Platelet-Activating Factor Acetylhydrolase Activity in more than 3000 Healthy Japanese," *Clinica Chimica Acta*. 312(1-2):179-183, 2000.
Kosaka T, et al., "Spectrophotometric Assay for Serum Platelet-Activating Factor Acetylhydrolase Activity," *Clinica Chimica Acta* (2000) 296(1-2):151-161.
Koenig W, et al., "Lipoprotein-Associated Phospholipase $A_2$ Adds to Risk Prediction of Incident Coronary Events by C-Reactive Protein in Apparently Healthy Middle-Aged Men from the General Population" *Circulation* (Oct. 2004) 110(14):1903-1908.
Balafa O, et al., "Urine of Patients with Nephritic Syndrome Contains the Plasma Type of PAF-Acetylhydrolase Associated with Lipoproteins," *Nephron Physiology* (2004)97(3):45-52.
Sarchielli P, et al., "Platelet-Activation Factor (PAF) in Internet Jugular Venous Blood of Migraine without Aura Patients Assessed During Migraine Attacks," *Cephalagia* (2004) 24(8):623-630.
U.S. Appl. No. 11/106,239, filed Apr. 14, 2005, Shou et al.
Karkabounas A., et al., "Quantitative Fluorescence Determination of Phospholipase $A_2$ and PAF Acetylhydrolase in Biological Fluids using High Performance Liquid Chromatography," *Chemistry and Physics of Lipids* (Jun. 2004)130(1):69-70.
Brites F, et al., "Paraoxonase 1 and Platelet-Activating Factor Acetylhydrolase Activities in Patients with Low HDL-Cholesterol Levels with or without Primary Hypertriglyceridemia," *Archives of Medical Research* (May 2004)35(3):235-240.
Kujiraoka T, et al., "Altered Distribution of Plasma PAF-AH between HDLs and other Lipoproteins in Hyperlipidemia and Diabetes Mellitus," *Journal of Lipid Research* (Oct. 2003) 44(10):2006-14.
Ito T, et al., "Serum PAF-Acetylhydrolase (PAF-AH) in Hepatobiliary Disease," *Japanese Pharmacology and Therapeutics* (2002) 30/Suppl. 2.

(Continued)

*Primary Examiner*—Ralph Gitomer
(74) *Attorney, Agent, or Firm*—Andrea V. Lockenour; Edward R. Gimmi; Sherry M. Knowles

(57) ABSTRACT

This invention relates to a method for determining the activity of Lp-PLA2 in a plurality of samples from animals. The invention also relates to a kit for determining Lp-PLA2 activity in a plurality of samples.

53 Claims, No Drawings

OTHER PUBLICATIONS

Unno, N et al., "Single Nucleotide Polymorphism ($G^{994} \rightarrow T$) in the Plasma Platelet-Activating Factor-Acetylhydrolase Gene is Associated with Graft Patency of Femoropopliteal Bypass," *Surgery* (2002) 132(1):66-71.

Dada, N, et al, "LP-PLA2: an emerging biomarker of coronary heart disease," *Expert Review of Molecular Diagnostics* (Jan. 2002) 2(1):17-22.

Ibe B, et al. "Platelet Activating Factor Acetylhydrolase Activity in Lamb Lungs is Up-Regulated in the Immediate Newborn Period," *Molecular Genetics and Metabolism* (Jan. 2000) 69(1):46-55.

Deigner H, et al., "Novel reversible, irreversible and fluorescent inhibitors of platelet-activating factor acetylhydrolase as mechanistic probes," *Atheroslcerosis* (May 1999) 144(1):79-90.

Kitsiouli E, et al. "Differential Determination of Phospholipase A(2) ane PAF-Acetylhydrolase in Biological Fluids Using Fluorescent Substrates," *Journal of Lipid Research* (Dec. 1999) 40(12):2346-2356.

Hendrickson HS, et al., "Intramolecularly Quenched BODIPY-Labeled Phospholipids Analogs in Phospholipase $A_2$ and Platelet-Activating Factor Acetylhydrolase assays and in Vivo Fluorescence Imaging," *Analytical Biochemistry* (Dec. 1999) 276(1):27-35.

Akiyama M, et al., "Identification of a Major PAF Acetylhydrolase in Human Serus/Plasma as a 43 KDa Glycoprotein Containing about 9 kDa Asparagine-Conjugated Sugar Chain(s)," *Journal of Biochemistry* (May 1998) 123(5):786-789.

Servillo L, et al., "Simultaneous Determination of Lysophospholipids by High-performance Liquid Chromatography with Fluorescence Detection," *Journal of Chromatography* (1997) 689(B):281-286.

Patrick DA, et al., "Reduced PAF-Acetylhydrolase Activity is Associated with Postinjury Multiple Organ Failure,", *Shock* (Mar. 1997)7(3):170-174.

Tsukioka K, et al., "Increased Plasma Level of Platelet-Activating Factor (PAF) and Decreased Serum PAF Acetylhydrolase (PAFAH) Activity in Adults with Bronchial Asthma," *Journal of Investigational Allergology and Clinical Immunology* (1996)6(1):22-29.

Balestrieri C, et al., "Measurement of Platelet-Activating Factor Acetylhydrolase Activity by Quantitative High-Performance Liquid Chromatography Determination of Courmarin-Derivatized 1-0-alkyl-2-sn-lysoglyceryl-3-phosphorylcholine," *Analytical Biochemistry* (Jan. 1996)233(2):145-50.

Riehl TE and Stenson WF., "Platelet-activating factor acetylhydrolases in Caco-2 cells and epithelium of normal and ulcerative colitis patients," *Gastroenterology* (1995)109(6):1826-1834.

Masaki A, et al., "New Serum PAF acetylhydrolase detection method used with the Blotting Method and Beta of $_3$Hacetyl-PAF," *Proceedings of Japanese Conference on the Biochemistry of Lipids* (1994)36:43-46.

Hemmings R, et al., "Platelet-Activating Factor Acetylhydrolase Activity in Peritoneal Fluids of Women with Endometriosis," *Obstetrics and Gynecology* (Feb. 1993)81(2):276-279.

Masao M et al., "On Development of a Measurement Method of Serum PAF Acetylhydrolase Activity Using an Automatic Analyser, and the Clinical Significance of Serum PAF Acetylhydrolase Defect," *Proceedings of Japanese Conference on the Biochemistry of Lipids* (1992)34:305-308.

Stafforini D., et al., "Platelet-Activating Factor Acetylhyrolase in Human erythrocytes," *Methods in Enzymology* (1991)197:411-425.

Kirschbaum B, "Platelet-Activating Factor Acetylhydrolase activity in the urine of patients with renal disease," *Clinical Chimica Acta* (Jun. 14, 1991)199(2):139-146.

Imaizumi T et al., "Activity of platelet-activating factor (PAF) acetylhydrolase in plasma from healthy habitual cigarette smokers" *Heart and Vessels* (1990)5(2):81-86.

Matsuzaki Masaharu, "Measurement Methods of Platelet Activating Factor (PAF) and PAF Acetylhydrolase (PAFAH) Activity," *SRL Hokan* (1989)13(3): 36-41.

Schindler PW, et al, "Fluorophore-labeled ether lipids: substrates for enzymes of the platelet-activating factor cycle in peritoneal polymorphonuclear leukocytes," *Analytical Biochemistry* (Nov. 1988) 174(2):477-84.

Miwa, M., et al, "Characterization of serum platelet-activating factor (PAF) acetylhydrolase. Correlation between deficiency of serum PAF acetylhydrolase and respiratory symptoms in asthmatic children." *Journal of Clinical Investigation* (Dec. 1988)82(6):1983-1991.

Masao Miwa, et al., "Serum platelet-activating factor (PAF) acetylhydrolase of children with bronchial asthma," *Japanese Journal of Inflammation* (1988)8(4):327-333.

Satoh Kei, et al, "Platelet-activating factor (PAF) acetylhydrolase and plasma lipoproteins: Relative distribution of the activity among lipoprotein classes," *Journal of Japan Atheroschlerosis Society* (1988)16(4):501-504.

Stafforini D, et al., "Human Plasma Platelet-Activating Factor Acetylhyrolase. Purification and Properties," *Journal of Biological Chemistry* (1987)262(9):4223-4230.

Kawamura Y, "A Simple Measurement of Plasma Platelet-Activating Factor (PAF) Acetylhydrolase, Normal Level Activity, and Distribution Among Lipoprotein Fractions," *Japanese Journal of Clincal Pathology* (Oct. 1987)35(10):1149-1153.

Pritchard PH, et al. "The Degradation of Platelet-Activating Factor in the Plasma of a Patient with Familial High Density Lipoprotein Deficiency (Tangier Disease)" *Blood* (1985) 66(6):1476-1478.

Caslake MJ, et al., "Lipoprotein-associated Phospholipase $A_2$ platelet-activating factor acetylhydrolase: a potential new risk factor for coronary artery disease," *Atherosclerosis* 150(2): 413-9, (Jun. 2000).

Z. Flegar-Mestric, et al., "Serum platelet-activating factor acetylhydriolase activity in patients with angiogrphically established cerebrovascular stenosis," *Clinical Chemistry and Laboratory Medicine, Processing of the IFFCC-FESCC European Congress, 15th* Barcelona, Spain: 369-372 (Jun. 1-5, 2003) (Publisher Monduzzi Editore, Bologna, Italy.

Akiyama, Masaki, A, et al., "Determination of Platelet-Activating Factor Acetylhydrolase Activity by Blotting, β-Radioluminescence, and Ultrahigh-Sensitivity Television Camera Detection" *Analytical Biochemistry* 21(2):295-299 (May 1994).

Karlan Research Products Corporation, Santa Rosa, CA, "Auto PAF-AH Serum (plasma) platelet-activating factor (PAF) acetylhydrolase assay—Instruction Manual" (2005).

Cayman Chemical, Ann Arbor, MI "PAF Acetylhydrolase Assay Kit" Catalog No. 760901.

DiaDexus Inc., "Enzyme Immunoassay for the Quantitative Determination of Lp-$PLA_2$ in Human Plasma and Serum" (Aug. 2005).

U.S. Appl. No. 11/106,239, Jul. 9, 2008, Shou, et al. Office Action.

Thirkettle, et al., *J. Antibiotics*, 53(7):664-669 (2000).

Thirkettle, *J. Antibiotics*, 53(7):733-735 (2000).

Boyd, et al., *Bioorg. Med. Chem. Lett.*, 10:395-398 (2000).

Boyd, et al., *Bioorg. Med. Chem. Lett.*, 10:2557-2561 (2000).

Tew, et al., *Biochem.*, 37:10087-10093 (1998).

Tew, et al., *Arteriosclerosis, Thrombosis Vasc. Biol.*, 16(4):591-599 (1996).

Stafforini D., et al. *The Journal of Biological Chemistry* (1997) 272(29):17895-17898.

Zalewski and MacPhee. *Arterioscler Thromb Vasc Biol.* (2005) 25:923-931.

* cited by examiner

HIGH THROUGHPUT ASSAY OF LP-PLA2 ACTIVITY

This application is a 371 National Phase entry of international application PCT/US04/16716 filed May 27, 2004, which claims priority to provisional application 60/473,777 filed May 28, 2003.

FIELD OF THE INVENTION

This invention relates generally to methods and materials for determining lipoprotein-associated phospholipase A2 (herein "Lp-PLA2") enzyme activity in samples from animals.

BACKGROUND OF THE INVENTION

Coronary heart disease (herein "CHD") is the leading cause of death in many industrial countries. Atherosclerosis is a form of arteriosclerosis or hardening of the arteries in which there is the progressive build-up of plaque containing cholesterol and lipids in blood arteries. This build-up is associated with an increased risk of heart disease and morbid coronary events. The build-up of plaque in the arteries is associated with an immune response that is triggered by damage to the endothelium. Initially, monocyte-derived macrophages accumulate at the damaged site, due to the immune response causing a migration and accumulation of smooth muscle cells which form fibrous plaque in combination with the macrophages, lipids, cholesterol, calcium salts and collagen. The growth of such lesions can eventually block the artery and restrict blood flow.

Lipoprotein-associated phospholipase A2 (Lp-PLA2), also known as PAF acetylhydrolase, is a secreted, calcium-independent member of the growing phospholipase A2 super-family (Tew, et al. (1996) *Arterioscler Thromb Vasc Biol.* 16(4):591-9; Tjoelker, et al. (1995) *Nature* 374(6522):549-53). It is produced by monocytes, macrophages, and lymphocytes and is found associated predominantly with LDL (~80%) in human plasma. The enzyme cleaves polar phospholipids, including sn-2 ester of 1-O-alkyl-2-scetyl-sn-glycero-3-phosphocholine, otherwise known as platelet-activating factor (herein "PAF") (Tjoelker, et al. (1995) *Nature* 374(6522):549-53).

Many observations have demonstrated a pro-inflammatory activity of oxidized LDL when compared with native unmodified lipoproteins. One of the earliest events in LDL oxidation is the hydrolysis of oxidatively modified phosphatidylcholine, generating substantial quantities of lysophosphatidylcholine (lyso-PC) and oxidized fatty acids. This hydrolysis is mediated solely by Lp-PLA2 (i.e., Lp-PLA2 hydrolyzes PAF to give lysophosphatidylcholine ["lyso-PC"] and acetate) (Stafforini, et al. (1997) *J Biol. Chem.* 272, 17895).

Lyso-PC is suspected to be a pro-inflammatory and pro-atherogenic mediator. In addition to being cytotoxic at higher concentrations, it is able to stimulate monocyte and T-lymphocyte chemotaxis, as well as induce adhesion molecule and inflammatory cytokine expression at more modest concentrations. Lyso-PC has also been identified as the component of oxidized LDL that is involved in the antigenicity of LDL, a feature that may also contribute to the inflammatory nature of atherosclerosis. Moreover, lyso-PC promotes macrophage proliferation and induces endothelial dysfunction in various arterial beds. The oxidized fatty acids that are liberated together with lyso-PC, are also monocyte chemoattractants and may also be involved in other biological activities such as cell signaling). Because both of these products of Lp-PLA2 hydrolysis are potent chemoattractants for circulating monocytes, Lp-PLA2 is thought to be responsible for the accumulation of cells loaded with cholesterol ester in the arteries, causing the characteristic "fatty streak" associated with the early stages of atherosclerosis.

Lp-PLA2 has also been found to be enriched in the highly atherogenic lipoprotein subfraction of small dense LDL, which is susceptible to oxidative modification. Moreover, enzyme levels are increased in patients with hyperlipidaemia, stroke, Type 1 and Type 2 diabetes mellitus, as well as in post-menopausal women. As such, plasma Lp-PLA2 levels tend to be elevated in those individuals who are considered to be at risk of developing accelerated atherosclerosis and clinical cardiovascular events. Thus, inhibition of the Lp-PLA2 enzyme would be expected to stop the build up of this fatty streak (by inhibition of the formation of lysophosphatidylcholine), and so be useful in the treatment of atherosclerosis. Furthermore, Lp-PLA2 can be used as a biomarker to determine if an animal is at risk for developing a disease associated with elevated Lp-PLA2 levels or elevated Lp-PLA2 activity.

Lp-PLA2 inhibitors inhibit LDL oxidation. Lp-PLA2 inhibitors may therefore have a general application in any disorder that involves lipid peroxidation in conjunction with the enzyme activity, for example in addition to conditions such as atherosclerosis and diabetes other conditions such as rheumatoid arthritis, stroke, myocardial infarction (Serebruany, et al. *Cardiology.* 90(2):127-30 (1998)); reperfusion injury and acute and chronic inflammation. In addition, Lp-PLA2 is currently being explored as a biomarker of coronary heart disease (Blankenberg, et al. *J Lipid Res.* 2003 May 1) and arteriosclerosis (Tselepis and Chapman. *Atheroscler Suppl.* 3(4):57-68 (2002)). Furthermore, Lp-PLA2 has been shown to play a role in the following disease: respiratory distress syndrome (Grissom, et al. *Crit Care Med.* 31(3): 770-5 (2003); immunoglobulin A nephropathy (Yoon, et al. *Clin Genet.* 62(2):128-34 (2002); graft patency of femoropopliteal bypass (Unno, et al. *Surgery* 132(1):66-71(2002); oral inflammation (McManus and Pinckard. *Crit Rev Oral Biol Med.* 11(2):240-58 (2000)); airway inflammation and hyperreactivity (Henderson, et al. *J Immunol.* 15; 164(6): 3360-7 (2000)); HIV and AIDS (Khovidhunkit, et al. *Metabolism.* 48(12):1524-31 (1999)); asthma (Satoh, et al. *Am J Respir Crit Care Med.* 159(3):974-9 (1999)); juvenile rheumatoid arthritis (Tselepis, et al. *Arthritis Rheum.* 42(2): 373-83 (1999)); human middle ear effusions (Tsuji, et al. *ORL J Otorhinolaryngol Relat Spec.* 60(1):25-9 (1998)); schizophrenia (Bell, et al. *Biochem Biophys Res Commun.* 29; 241(3):630-59 (1997)); necrotizing enterocolitis development (Muguruma, et al. *Adv Exp Med Biol.* 407:379-82 (1997)); and ischemic bowel necrosis (*Pediatr Res.* 34(2): 237-41 (1993)).

Lp-PLA2 activity from human samples has been measured using spectrophotometric activity and fluorogenic activity assays (Cayman Chemical Company, AtheroGenics, Inc. and Karlan Research Products). See also Kosaka, et al. *Clin Chem Acta* 296(1-2):151-61 (2000) and Kosaka, et al. *Clin Chem Acta* 312(1-2):179-83 (2001). However, these methods may be insensitive when inhibitor to Lp-PLA2 is present, particularly when the inhibitor is administered to an animal prior to obtaining a sample from the animal. The assay of the current invention has been shown to demonstrate a correlation between Lp-PLA2 inhibitor concentration in a sample and Lp-PLA2 activity. Lp-PLA2 activity measured over time in patients treated with inhibitor correlated with the pharmacokinetic profile of the inhibitor.

Radiolabeled PAF has been used in low throughput assays for Lp-PLA2 activity. Tselepis, et al. *Arterioscler Thromb Vasc Biol.* 15(10):1764-73 (1995) and Min, et al. *Biochemistry,* 40(15):4539-4549 (2001). However, these methods have not been developed as high throughput methods and therefore are not useful for large scale studies compared with the present invention. Lp-PLA2 concentration from human samples has been measured using an ELISA assay using high throughput methods. A strong correlation has been found between the current activity assays available and the mass or ELISA assay. However, the mass or ELISA assay is probably not sensitive to detecting Lp-PLA2 inhibitors in samples. In order to measure Lp-PLA2 activity with or without inhibitor in a large-scale study or to screen a plurality of samples for Lp-PLA2 as a selected biomarker, a high throughput activity protocol is required. Accordingly, a method for determining LP-PLA2 activity from a plurality of samples is greatly needed.

SUMMARY OF THE INVENTION

Thus, one object of the present invention is to provide a method for determining lipoprotein-associated phospholipase A2 (Lp-PLA2) enzyme activity in samples comprising the steps of preparing a solution comprising labeled platelet-activating factor (PAF); contacting each of a plurality of tissue samples with the solution of the preparing step and with a sequester molecule of PAF to form a PAF-sequester molecule complex; removing said PAF-sequester molecule complex; and detecting an Lp-PLA2 activity.

Another object of the present invention is to provide a kit for determining Lp-PLA2 enzyme activity in a plurality of samples comprising platelet-activating factor (PAF); a sequester molecule for PAF; and a precipitation solution.

DETAILED DESCRIPTION OF THE INVENTION

Glossary

A "sequester molecule" as used herein is any molecule capable of forming a complex with a second molecule either alone or in combination with other molecules or co-factors in such a way as to facilitate the separation of the second molecule from other molecules and/or solution. For instance, a sequester molecule may be a protein that attaches to a second molecule to make it precipitate from solution or it may create a charge on the second molecule making it more likely to be drawn to a positive or negative electrode. Examples of sequester molecules to PAF comprise, but are not limited to, bovine serum albumin (herein "BSA") and human serum albumin.

A "PAF-sequester molecule complex" as used herein is PAF in association with a sequester molecule so that the sequester molecule has contacted PAF to facilitate PAF's separation from other molecules and/or solution. As an example, PAF may form a complex with BSA which can be precipitated from solution. PAF-sequester molecule complex may comprise both uncleaved PAF and lyso-PC in complex with the sequester molecule. PAF-BSA complex is an example of a PAF-sequester molecule complex.

"Lp-PLA2 enzyme activity" as used herein includes, but is not limited to, any enzyme activity of Lp-PLA2. This activity may include, but is not limited to, the enzyme binding substrate, releasing product, and/or hydrolyzing phospholipids or other molecules.

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may comprise amino acids other than the 20 gene encoded amino acids. "Polypeptide(s)" comprise those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may comprise many types of modifications. Modifications can occur anywhere in a polypeptide, including the peptide backbone, the amino acid side-chains, and the amino or carboxyl termini. Modifications comprise, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, PROTEINS-STRUCTURE AND MOLECULAR PROPERTIES, 2nd Ed., T. E. Creighton, W. H. Freeman and Company, New York (1993) and Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York (1983); Seifter et al., *Meth. Enzymol.* 182:626-646 (1990) and Rattan et al., Protein Synthesis: Posttranslational Modifications and Aging, Ann. N.Y. Acad. Sci. 663: 48-62 (1992). Polypeptides may be branched or cyclic, with or without branching. Cyclic, branched and branched circular polypeptides may result from post-translational natural processes and may be made by entirely synthetic methods, as well.

"Precipitation solution" as used herein is any solution capable of precipitating PAF-sequester molecule complex from solution. A precipitation solution may comprise, but is not limited to, trichloroacetic acid ("TCA"), non-ionic polymers such as dextrans or polyethelene glycols, or metal ions such as $Mn^{2+}$, $Fe^{2+}$, $Co^{2+}$, $Ni^{2+}$, $Zn^{2+}$, $Cd^{2+}$, $Ca^{2+}$, $Ba+2$, $Mg+2$, $Pb+2$, $Ag+$, $Hg^{2+}$, and $Pb^{2+}$. The precipitation solution may use isoelectric recipitation, thus changing the salt content of the solution to facilitate precipitation. The recipitation solution may change dielectric constant of the solution with the addition of an organic solvent. Organic solvents that may be used in a precipitation solution may include, but are not limited to, 2 methyl-2,4pentane diol (MPD), dimethyl sulfoxide (DMSO), acetone and ethanol. The precipitation solution may also change the pH of the solution comprising PAF-sequester molecule to facilitate precipitation.

"Filtration" or "filtering" as used herein includes, but in not limited to, the removal of any substance from a solution and may comprise passing a solution containing the substance to be removed through filter paper, Whatman paper, cheese cloth, or a column that selectively removes said substance from solution based on its physical and/or chemical characterisics. The substance to be removed may include PAF-sequester molecule complex. Physical and chemical characteristics that may be used to remove a substance through filtration may include, but are not limited to, ionic charge, size, weight, polarity, and/or chemical moieties associated with the substance that make it likely to bind to the material filling a column. Filtration may comprise using gravity, vacuum, and/or centrifugation to facilitate the removal of said substance from solution.

"Scintillation cocktail" as used herein is a mixture of solutes and solvents, typically containing an organic solvent capable of solubilizing and maintaining a uniform suspension of a sample for liquid scintillation. The process of liquid scintillation involves the detection of beta decay within a sample via capture of beta emissions. A scintillation cocktail mixture is designed to capture the beta emission and transform it into a photon emission which can be detected via a photomultiplier tube within a scintillation counter. Several scintillation cocktails are commercially available. It is understood that a modification of the composition of the scintillation cocktail can effect and/or optimize the detectable reading from liquid scintillation depending on the sample.

"Tissue(s)" as used herein comprises serum, cell lysate, tissue lysate, urine, blood plasma, plaque, monocytes, or macrophage cells. These tissues can be from humans, non-human mammals or other animals that express Lp-PLA2, homologs or orthologs thereof.

The symbol "*" used in the formulas presented herein indicates the mathematical function of multiplication.

Lp-PLA2 is a known hydrolyzer of phospholipids. Lp-PLA2 can cleave phospholipids at the sn-2 position to create lysophosphatidylcholine (lyso-PC) and oxidized fatty acids. PAF has a two-carbon acyl group at the sn-2 position; therefore, when PAF is hydrolyzed by $Lp-PLA_2$, the short acyl group is cleaved as water soluble acetate from the remainder of the molecule, which is lysophosphatidylcholine (lyso-PC). Acetate is water soluble at condition under which lyso-PC can be precipitated from an aqueous solution. For instance, a sequester molecule such as BSA can associate with the uncleaved PAF and/or lyso-PC forming a complex. This complex can then be removed from solution leaving the small water soluble molecule, in this case acetate, in solution. It is understood in the art that several methods exist for detecting the amount of small water soluble molecule remaining in solution after precipitation. For instance, acetate may be radiolabeled prior to cleavage and detected by liquid scintillation. Alternatively, the amount of phosphocholine precipitated out of solution can be detected to measure Lp-PLA2 activity.

An embodiment of the present invention is to provide a method for determining Lp-PLA2 enzyme activity in samples comprising the steps of preparing a solution comprising labeled PAF; contacting each of a plurality of tissue samples with the solution of the preparing step and with a sequester molecule of PAF to form a PAF-sequester molecule complex; removing said PAF-sequester molecule complex; and detecting an Lp-PLA2 activity. In one aspect, the PAF-sequester molecule may be removed by precipitation, centrifugation, and/or filtration. In another aspect, at least one sample is taken from an animal that has been administered with Lp-PLA2 inhibitor.

A further embodiment provides that contacting tissue samples with the solution of the preparing step and with a sequester molecule of PAF to form a PAF-sequester molecule complex, may be performed simultaneously or as separate steps in any order.

Yet another embodiment of the present invention is to provide a method for determining lipoprotein-associated phospholipase A2 (Lp-PLA2) enzyme activity in a plurality of samples comprising the steps of: preparing a solution comprising labeled platelet-activating factor (PAF); first contacting each of the plurality of tissue samples with the solution of the preparing step; second contacting each of the solutions of the first contacting step with a sequester molecule of PAF to form PAF-sequester molecule complex; contacting said PAF-sequester molecule complex with a precipitation solution to form a precipitate; separating the precipitate from the supernatant; and detecting Lp-PLA2 activity. In one aspect of the invention at least one sample comprise blood. In one aspect, the PAF-sequester molecule may be separated by centrifugation, and/or filtration. In another aspect, at least one sample is about 5 µL in volume. In another, each of the plurality of samples is aliquoted into microfuge tubes or wells in a microtitre plate.

In another aspect of the invention, the labeled PAF is radiolabeled. The labeled PAF may be tritiated or labeled with $^{14}C$. In another aspect of the invention, labeled PAF comprises at most 20% of the PAF in the solution, and in another aspect, it may be about 0.4% to about 2.0% of the PAF solution. PAF may have a concentration of at least about 20 µM in solution. In another aspect of the invention, PAF is a substrate for Lp-PLA2. In another aspect, the PAF is in a buffered solution. The buffered solution may comprise 4-2-hydroxyethyl)-1-piperazineethane sulfonic acid (HEPES), sodium chloride (NaCl), and ethylenediaminetetraacetic acid (EDTA).

In another aspect of the invention, a method is provided comprising mixing the solution of the preparing step and sample for at least 5 seconds and incubating at about 21° C. for at least about 1 minute. Sample may be incubated with the solution of the preparing step for about 5 minutes.

In another aspect of the invention, the sequester molecule of a contacting step is exogenous bovine serum albumin (BSA), but it may also be endogenous human serum albumin. The temperature of the BSA may be less than about 10° C., and it may be about 4° C. In another aspect, the BSA is at a concentration of about 50 mg/mL. In yet another aspect, the sequester molecule and sample are incubated at less than 10° C. for at least about 1 minute.

In another aspect of the present invention, the precipitation solution comprises TCA. In another aspect, the precipitation solution comprising TCA is less than about 10° C. In another aspect, the TCA has a concentration of about 56% volume/volume with water. In another aspect, the solution of the second contacting step is incubated with the solution comprising TCA for at least 1 minute. The precipitate may be separated from the supernatant by centrifugation at at least about 6,000 g for about 5 minutes at less than about 10° C. In another aspect, centrifugation is conducted at about 4° C. for about 15 minutes.

In another aspect of the invention, a buffered solution is aliquoted into at least two containers for use as total count reactions or blank reactions. These containers may be microfuge tubes or wells of a microtitre plate. In another aspect, the buffered solution is the same as the solution of the preparing step wherein no PAF has been added to the solution. In another aspect of the present invention, the volume of buffered solution aliquoted for total count reactions and blank reaction are the same as the volume of sample used for each sample reaction. The solution of the preparing step and the sequester molecule may be added to aliquots of buffered solution for use as blank reactions at the same volume, concentration, contacting, and precipitating conditions as sample. In another aspect of the invention, at least two total count reaction aliquots are contacted with about the same volume of solution of the preparing step and a substitute solution for the sequester molecule wherein the substitute solution does not contain sequester molecule. A buffered solution or distilled water may be added to each total count reaction at about the same volume as a solution comprising sequester molecule, which is added to samples and/or blank reactions.

In another aspect of the present invention, a portion of each sample supernatant, blank reaction, and total count reaction are aliquoted into separate containers. Each aliquot of supernatant, blank reaction, and total count reaction may be contacted with a scintillation cocktail and counted in a scintillation counter for at least about 1 minute.

In another aspect of the present invention, $CPM_{TotalCounts}$ are calculated as the net average count of total count reactions using the following formula:

$$CPM_{TotalCounts}=(CPM_{NetTotalCounts}*V_{RT})/(V_{SA})$$

Where $CPM_{NetTotalCounts}$=the net average count in aliquots of supernatants from total count reactions;

$V_{RT}$=total volume of final reaction solution prior to centrifugation; and $V_{SA}$=volume of supernatant from total count reactions aliquoted for scintillation counting.

In another aspect, Lp-PLA2 activity in each supernatant is calculated using the following formula:

$$Lp\text{-}PLA2\ \text{activity(nmoles/min/ml)}=S*(CPM_{sample}-CPM_{Blanks})*V_{ST}/(CPM_{TotalCounts}*V_{SA}*V*T)$$

Where S=total amount of PAF (nmoles) in the solution of the preparing step;

$CPM_{sample}$=the average count of supernatants from each sample;

$CPM_{Blanks}$=the average count of supernatants from blank reactions;

$V_{ST}$=sum volume of supernatants;

$CPM_{TotalCounts}$=the average count from total count reactions;

$V_{SA}$=volume of each supernatant aliquoted for scintillation counting;

V=total volume of sample (μL) aliquoted in the first contacting step; and

T=total amount of time (minutes) for the first contacting step.

In another aspect of the invention, a buffered solution is aliquoted into at least two containers for use as blank reaction. These containers may be microfuge tubes or wells of a microtitre plate. In another aspect, the buffered solution is the same as the solution of the preparing step wherein no PAF has been added to the solution. In another aspect of the present invention, the volume of buffered solution aliquoted for a blank reaction is the same as the volume of sample used for each sample reaction. The solution of the preparing step may be added to aliquots of buffered solution for use as blank reactions at the same volume, concentration, contacting, and precipitating conditions as sample.

In another aspect of the present invention, an aliquot of the solution of the preparing step is contacted with at least one blank reaction for use as total added counts. The volume of the aliquot of solution of the preparing step may be between about 1 μL to about 20 μL, or it may be about 10 μL. In another aspect of the present invention, each aliquot of supernatant, blank reactions and total added counts is contacted with a scintillation cocktail and counted in a scintillation counter for at least about 1 minute.

In another aspect of the present invention, $CPM_{TotalAddedCounts}$ is calculated as the volume-adjusted net average count of total added count reactions using the following formula:

$$CPM_{TotalAddedCounts}=(CPM_{NetSpikedCounts}*V_{PAF})/(V_{Spiked})$$

Where $CPM_{NetSpikedCounts}$=the net average count of supernatants from total added counts;

$V_{PAF}$=volume of the solution of the preparing step added in the first contacting step;

$V_{Spiked}$=volume of the solution of the preparing step added to the supernatants from the blank reactions for use as total added counts.

In another aspect of the present invention, Lp-PLA2 activity is calculated in each supernatant using the following formula:

$$Lp\text{-}PLA2\ \text{activity(nmoles/min/ml)}=S*(CPM_{sample}-CPM_{Blanks})*V_{ST}/(CPM_{TotalAddedCounts}*V_{SA}*V*T)$$

Where S=total amount of PAF (nmoles) in the solution of the preparing step;

$CPM_{sample}$=the average count of supernatants from each sample;

$CPM_{Blanks}$=the average count of supernatants from blank reactions;

$V_{ST}$=sum volume of supernatants;

$CPM_{TotalAddedCounts}$=the average count from total added counts;

$V_{SA}$=volume of each supernatant aliquoted for scintillation counting;

V=total volume of sample (μL) aliquoted in the first contacting step; and

T=total amount of time (min) for the first contacting step.

In another embodiment of the invention, a kit is provided for determining lipoprotein-associated phospholipase A2 (Lp-PLA2) enzyme activity in a plurality of blood samples comprising platelet-activating factor (PAF); a sequester molecule for PAF; and a solution comprising TCA.

The following examples illustrate various aspects of this invention. These examples do not limit the scope of this invention which is defined by the appended claims.

EXAMPLES

Example 1

Titration of BSA Concentration for Sequestering and Precipitation

The concentration of BSA and contact time with free $^3$H-PAF was examined. $^3$H-PAF at a concentration of 200 μM in buffered solution was contacted with BSA at a concentration of 1.04 mg/mL-16.67 mg/mL for 5 minutes or overnight BSA and PAF complexes were then precipitated with 7.78% TCA and pelleted with centrifugation at 6,000 g for 15 minutes at 4° C. The percentage of free $^3$H-PAF remaining in solution was measured in the supernatants with scintillation counting. As shown in Table 1, the percentage of free PAF removed from solution by precipitation increased with increasing BSA concentrations and prolonged incubation periods.

TABLE 1

Titration of BSA Concentration for Sequestering PAF

| Concentration of BSA | (%) Percentage of $^3$H-PAF remaining in solution after precipitation Time in contact with $^3$H-PAF before precipitation | |
| --- | --- | --- |
| (mg/mL) | 5 Minutes | Overnight |
| 0 | 100 | 100 |
| 1.04 | 29.91 | 28.99 |
| 2.08 | 12.25 | 10.16 |
| 4.17 | 2.00 | 1.42 |
| 8.33 | 1.55 | 1.01 |
| 16.67 | 1.19 | 0.95 |

Example 2

Optimization of TCA Precipitation Time and Temperature $^3$H-PAF in buffered solution was sequestered with BSA at a concentration of 16.67 mg/mL and incubated for 5 minutes on ice. PAF was precipitated with either ice cold TCA at 7.78% and incubated on ice for 15 minutes, or with 7.78% TCA at room temperature followed by incubation at room temperature for 5, 10 or 20 minutes. As shown in Table 2, ice-cold TCA followed by incubation on ice for 15 minutes caused the smallest percentage of PAF to be left in solution.

TABLE 2

| | Precipitation with TCA | |
| --- | --- | --- |
| Time in contact with | (%) Percentage of $^3$H-PAF remaining in solution after precipitation Temperature | |
| TCA (minutes) | Ice | Room Temperature |
| 5 | Not done | 1.28 |
| 10 | Not done | 1.43 |
| 15 | 1.09 | Not done |
| 20 | Not done | 1.67 |

Example 3

Centrifugation of PAF-BSA Complexes $^3$H-PAF in buffered solution was sequestered with BSA at a concentration of 16.6 mg/mL and incubated on ice for 5 minutes. PAF-BSA complex was precipitated with ice-cold TCA at 7.78% and incubated on ice for 15 minutes. Precipitated PAF-BSA complexes were centrifuged using a microfugal force from 800 g to 13,000 g. The percentage of $^3$H-PAF remaining in solution after centrifugation was measured. About 1.3% to about 2% of PAF-BSA complex remained in solution using a microfugal force of less than 5,000 g. When the microfugal force was increased to at least 6,000 g only about 1.1% or less of PAF-BSA complex remained in solution.

Example 4

Lp-PLA2 Activity as Influenced by Reaction Temperature Over Time

Lp-PLA2 was reacted with PAF over 30 minutes at both 37° C. and room temperature (~21° C.), and the activity was measured as the radioactivity (i.e., Disintegration Per Minute or DPM) of the products released from the PAF by scintillation counting. Reaction rates were linear over a 30-minute period regardless of reaction temperatures. Reactions conducted at 37° C. showed greater Lp-PLA2 activity than those at room temperature. Lp-PLA2 activity at 30 minutes was approximately 80,000 DPM for reaction at 37° C. and 40,000 DPM for reaction at room temperature.

Example 5

Cocktails for Scintillation Counting of the Reaction Products

Three commercially available scintillation cocktails were used to measure the radioactivity of PAF in a buffered solution. MicroScint-20®, MicroScint-40® and Scintisafe® were tested. Counts per minute (CPM) of 40 µL of the PAF solution were higher with MicroScint-20 than MicroScint-40. In addition, counting of 80 µL of the reaction products in MicroScint-40 failed to double the radioactivity of 40 µL of the same reaction products in MicroScint-20. Similarly, MicroScint-20 showed significantly better counting efficiency than ScintiSafe-30%.

Example 6

Linearity of Plasma Dilution for Measurements of Lp-PLA2 Activity

Lp-PLA2 activity was measured from dilutions of a human plasma sample in a 5-minute reaction with $^3$H-PAF at room temperature. Reactions were terminated with sequestering of the PAF substrates with ice-cold 16.67 mg/mL BSA. The PAF-BSA complexes were precipitated with ice-cold 7.78% TCA and pelleted at 6,000 g for 15 minutes at 4° C. Reactions products in supernatants were measured by scintillation counting using MicroScint-20 cocktail. Between 0.1 µL/reaction and 5 µL/reaction of plasma were used in separate reactions. Measured Lp-PLA2 activity values in a human plasma sample were linearly proportional to amounts of human plasma added to the reactions.

Example 7

Lp-PLA2 Activity Assay for a Plurality of Samples Using a Microplate

Assay buffer was prepared and stored at room temperature with the following specifications: 100 mM HEPES, pH 7.4; 150 mM NaCl; and 5 mM EDTA.

$^3$H-PAF solution was prepared for 100 reactions by aliquoting 480 µL $^3$H-PAF (10 µM=0.1 mCi/ml at 10.0 Ci/mmol) and 24.6 µL of C16-PAF (also known as "1-hexadecyl-2-acetyl-sn-glycero-3-phosphocholine") (5.0 mg/ml; MW: 524) into a tube. The two solutions were mixed and air dried in a hood. Dried pellets were re-suspended in 12.0 mL of assay buffer creating $^3$H-PAF solution of 20 µM PAF (i.e. $^3$H-PAF at 0.4 µM and cold C16-PAF at 19.6 µM).

For the Lp-PLA2 activity assay, 5 µL of assay buffer (for Total counts and Blanks; n=8) or plasma samples in duplicates was aliquoted into a 96-well plate. Each plate was sealed with a tape to prevent evaporation. Plates were equilibrated to 21° C.

One hundred microLiters of the $^3$H-PAF solution was added to each well, mixed and incubated at 21° C. for 5 minutes. Ice-cold BSA solution (50 µL of a 50 mg/mL BSA in aqueous solution) was added to each well, with the exception of samples used as Total counts, to which 50 μL of water was added instead. The solutions were then mixed and incubated in a refrigerator for 5 minutes.

Ice-cold TCA solution (25 μL of a 56% v/v solution) was added to each well, mixed and incubated in a refrigerator for 15 minutes. The plate was then centrifuged at 6,000 g for 15 minutes at 4° C. A 45 μL aliquot of each supernatant was transferred to a 96-well polystyrene plate.

$^3$H-PAF solution (10 μL) was added to six wells to serve as Total counts. MicroScint-20 scintillation cocktail (200 μL) was added to each well and the plates were covered with tape and vortex mixed at maximum speed for 10 minutes. Static was removed from the plates by wiping with a wet tissue and drying with another clean one. Sample counts were obtained for each sample using a TopCount scintillation counter for 2 minutes each.

Lp-PLA2 activity was calculated using the following formula:

$$Lp\text{-}PLA2\ activity(nmoles/min/ml) = 32*(CPM_{45\ \mu l\text{-}supe} - CPM_{Blanks})/(CPM_{10\ \mu l\text{-}spiking} - CPM_{Blanks})$$

Where $CPM_{45\ \mu l\text{-}supe}$ is the average count froma each sample $CPM_{Blanks}$ is the average count of the Blanks $CPM_{10\ \mu l\text{-}spiking}$ is the average count of the Total Counts Example 8

Lp-PLA2 Activity in Humans Treated with Lp-PLA2 Inhibitor

Plasma samples were collected from healthy volunteers at baseline and scheduled timepoints after dosing up to 144 hours after dosing with either Lp-PLA2 inhibitor or placebo. Plasma samples were assayed for Lp-PLA2 activity as described in Example 7. Significant inhibition of Lp-PLA2 activity (>85%) in drug-treated volunteers was observed from about 1 hour after administration of inhibitor until about 6 to about 8 hours after administration of inhibitor. This measured inhibition correlated with pharmacokinetic data of the inhibitor. In contrast, no significant decrease in Lp-PLA2 activity was detected in volunteers who received placebo. When plasma samples were assayed with a spectrophotometric assay, only about 30% inhibition of Lp-PLA2 was detected from the same samples from volunteers treated with inhibitor.

Example 9

Validation of the High-Throughput Radiometric Lp-PLA2 Activity Measurements

The methods of this invention relating to high throughput measurement of Lp-PLA2 activity using radiolabeled substrate as described in Example 7 were validated by comparison of intra-assay activity measurements as well as a comparison of activity measurements determined from extraction methods. The methods of this invention showed excellent performance characteristics with a Limit of Detection ("LOD") of 0.2 nmoles/min/mL and a linear dynamic range of about 100 fold (0.5-48.5 nmoles/min/ml). The Limit of Quantitation ("LOQ") estimate and the lower end of the linear dynamic range were the same.

In addition, Lp-PLA2 activity values determined using the methods of the invention are highly correlated with those determined with the extraction procedures in when compared with samples from two clinical trials Trial A (n=68) and Trial B (n=48). In addition, it offers a number of advantages over an extraction protocol, including small plasma sample volume, no radioactive organic waste and much higher throughput which can be further increased with automation if necessary. The variance components analyses for the high throughput Lp-PLA2 activity assay using radiolabeled substrate (Example 7) of this invention showed that the estimated within plate (intra-assay) variance component ("CV") met the validation criteria (Variance Components Study intra-assay CV is about 11.2%; <15% criteria). The inter-assay CV estimate also met the validation criteria (inter-assay CV is about 12.9%; <20% criteria). The estimation of the reduction of the inter-assay variability when the number of blank serum and total count wells were increased from 2 each to 4 each was approximately 1.5% with the additional blank serum and total count wells. A separate analysis of the variability between rows from different pipette tips showed a contribution of approximately 13% of the intra-assay CV estimate.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

The invention claimed is:

1. A method for determining an Lp-PLA2 enzyme activity in a plurality of samples comprising the steps of preparing a solution comprising labeled PAF; contacting each of a plurality of tissue samples with the solution of the preparing step and with a sequester molecule of PAF, wherein said sequester molecule is exogenous BSA, to form a PAF-sequester molecule complex; removing said PAF-sequester molecule complex; and detecting an Lp-PLA2 activity by measuring the amount of PAF cleaved by said Lp-PLA2 enzyme wherein said amount of cleaved PAF determines Lp-PLA2 activity.

2. The method of claim 1 wherein the contacting step comprises first contacting each of the plurality of samples with the solution of the preparing step; second contacting each of the solutions of the first contacting step with a sequester molecule of PAF, wherein said sequester molecule is exogenous BSA, to form PAF-sequester molecule complex; the removing step comprises contacting said PAF-sequester molecule complex with a precipitation solution to form a precipitate and a supernatant; and the detecting step comprises separating the precipitate from the supernatant; and detecting Lp-PLA2 activity.

3. The method of claim 1 or 2, wherein the removing step comprises filtering the PAF-sequester molecule.

4. The method of claim 1 or 2, wherein at least one sample comprises blood.

5. The method of claim 1 or 2, wherein at least one sample is selected from the group consisting of serum, cell lysate, tissue lysate, urine, or blood plasma.

6. The method of claim 1 or 2, wherein at least one sample is from human.

7. The method of claim 1 or 2, wherein at least one sample is about 5 μL in volume.

8. The method of claim 1 or 2, further comprising aliquoting each of the plurality of samples into microfuge tubes.

9. The method of claim 1 or 2, further comprising aliquoting each of the plurality of samples into a well in a microtitre plate.

10. The method of claim 1 or 2, wherein the labeled PAF is radio-labeled.

11. The method of claim 10, wherein the labeled PAP is tritiated.

12. The method of claim 10, wherein the labeled PAP is labeled with $^{14}C$.

13. The method of claim 1 or 2, wherein the labeled PAF comprises at most about 20% of the PAF in the solution used in the preparing step.

14. The method of claim 1 or 2, wherein the labeled PAF comprises about 2.0% of the PAF in the solution used in the preparing step.

15. The method of claim 1 or 2, wherein the total concentration of PAF in solution of the preparing step is at least about 20 µM.

16. The method of claim 1 or 2, wherein PAF is a substrate for Lp-PLA2.

17. The method of claim 1 or 2, wherein the solution comprising labeled and non-labeled PAF is a buffered solution.

18. The method of claim 17, wherein the buffered solution comprises HEPES, sodium chloride (NaCl), and ethylenediaminetetraacetic acid (EDTA).

19. The method of claim 1, further comprising mixing the solution of the preparing step and each sample for at least about 5 seconds.

20. The method of claim 19, further comprising incubating the solution of the preparing step with each sample at about 21° C. for at least about 1 minute.

21. The method of claim 20, wherein each sample is incubated with the solution of the preparing step for about 5 minutes.

22. The method of claim 1 or 2, wherein PAF-sequester molecule complex comprises uncleaved PAF-sequester molecule complex and lysophosphotidylcholine(lyso-PC)-sequester molecule complex.

23. The method of claim 1 or 2, wherein the BSA is less than about 10° C.

24. The method of claim 1 or 2, wherein the BSA is about 4° C.

25. The method of claim 1 or 2, wherein the BSA has a concentration of about 50 mg/mL.

26. The method of claim 2, wherein the solution of the first contacting step and the sequester molecule are incubated at less than about 10° C. for at least about 1 minute.

27. The method of claim 2, wherein the precipitation solution comprises TCA.

28. The method of claim 27, wherein the precipitation solution comprising TCA is less than about 10° C.

29. The method of claim 27, wherein the TCA has a concentration of 56% volume/volume with water.

30. The method of claim 27, wherein the TCA is incubated with the solution of second contacting step for at least about 1 minute.

31. The method of claim 27, wherein the precipitate is separated from the supernatant by centrifugation.

32. The method of claim 31, wherein centrifugation is conducted at at least 6,000 g for at least about 5 minutes at less than about 10° C.

33. The method of claim 31, wherein the centrifugation is conducted at 4° C. for about 15 minutes.

34. The method of claim 2, further comprising aliquoting a buffered solution into at least two containers for use as total count reactions or blank reactions.

35. The method of claim 34, wherein the containers are microfuge tubes or wells of a microtitre plate.

36. The method of claim 34, wherein the buffered solution is the same as the solution of the preparing step wherein no PAF has been added to the solution.

37. The method of claim 34, wherein the volume of buffered solution is about the same as the volume of sample used in each of the plurality of samples.

38. The method of claim 34, further comprising, contacting at least one blank reaction with about the same volume and concentration of solution of the preparing step and sequester molecule and contacting at least two total count reaction aliquots with about the same volume of solution of the preparing step and a substitute solution for the sequester molecule wherein the substitute solution does not contain sequester molecule.

39. The method of claim 38, further comprising aliquoting a portion of each sample supernatant, blank reaction, and total count reaction into separate containers.

40. The method of claim 39, further comprising contacting a scintillation cocktail to each aliquot of supernatant, blank reaction, and total count reaction.

41. The method of claim 40, further comprising counting the scintillation cocktail and supernatant, blank reaction, and total count reaction in a scintillation counter for at least about 1 minute.

42. The method of claim 41, further comprising calculating $CPM_{TotalCounts}$ as the net average count of total count reactions using the following formula:

$$CPM_{TotalCounts}=(CPM_{NetTotalCounts}*V_{RT})/(V_{SA})$$

Where $CPM_{NetTotalCounts}$=the net average count in aliquots of supernatants from total count reactions;

$V_{RT}$=total volume of final reaction solution prior to centrifugation; and $V_{SA}$=volume of supernatant from total count reactions aliquoted for scintillation counting.

43. The method of claim 42 further comprising, calculating Lp-PLA2 activity in each supernatant using the following formula:

$$Lp\text{-}PLA2 \text{ activity(nmoles/min/ml)}=S*(CPM_{sample}-CPM_{Blanks})*V_{ST}/(CPM_{TotalCounts}*V_{SA}*V*T)$$

Where S=total amount of PAF (nmoles) in the solution of the preparing step;

$CPM_{sample}$=the average count of supernatants from each sample;

$CPM_{Blanks}$=the average count of supernatants from blank reactions;

$V_{ST}$=sum volume of supernatants;

$CPM_{TotalCounts}$=the average count from total count reactions;

$V_{SA}$=volume of each supernatant aliquoted for scintillation counting;

V=total volume of sample (µL) aliquoted in the first contacting step; and

T=total amount of time (minutes) for the first contacting step.

44. The method of claim 34, further comprising contacting an aliquot of the solution of the preparing step to at least one blank reaction for use as total added counts.

45. The method of claim 44, wherein the volume of the aliquot of solution of the preparing step is between about 1 µL to about 20 µL.

46. The method of claim 44, wherein the volume of the aliquot of solution of the preparing step is about 10 µL.

47. The method of claim 44, further comprising contacting a scintillation cocktail to each aliquot of supernatant, blank reactions and total added counts.

48. The method of claim 47, further comprising counting the scintillation cocktail and supernatant, scintillation cocktail and blank reactions, and scintillation cocktail and total added counts in a scintillation counter for at least about 1 minute.

49. The method of claim 48, further comprising calculating $CPM_{TotalAddedCounts}$ as the volume-adjusted net average count of total added count reactions using the following formula:

$$CPM_{TotalAddedCounts} = (CPM_{NetSpikedCounts} * V_{PAF})/(V_{Spiked})$$

Where $CPM_{NetSpikedCounts}$=the net average count of supernatants from total added counts;

$V_{PAF}$=volume of the solution of the preparing step added in the first contacting step;

$V_{Spiked}$=volume of the solution of the preparing step added to the supernatants from the blank reactions for use as total added counts.

50. The method of claim 49 further comprising, calculating Lp-PLA2 activity in each supernatant using the following formula:

$$Lp\text{-}PLA2\ activity(nmoles/min/ml) = S*(CPM_{sample} - CPM_{Blanks})*V_{ST}/(CPM_{TotalAddedCounts}*V_{SA}*V*T)$$

Where S=total amount of PAF (umoles) in the solution of the preparing step;

$CPM_{sample}$=the average count of supernatants from each sample;

$CPM_{Blanks}$=the average count of supernatants from blank reactions;

$V_{ST}$=sum volume of supernatants;

$CPM_{TotalAddedCounts}$=the average count from total added counts;

$V_{SA}$=volume of each supernatant aliquoted for scintillation counting;

V=total volume of sample (μL) aliquoted in the first contacting step; and

T=total amount of time (min) for the first contacting step.

51. The method of claim 1 or 2, wherein at least one sample is taken from an animal that has been administered with Lp-PLA2 inhibitor.

52. A kit for determining Lp-PLA2 enzyme activity in a plurality of samples comprising PAF; a sequester molecule for PAF; and a precipitation solution, wherein said sequester molecule is exogenous BSA.

53. The kit of claim 52, wherein the precipitation solution comprises TCA.

* * * * *